United States Patent
Chambliss

(10) Patent No.: US 11,612,524 B2
(45) Date of Patent: Mar. 28, 2023

(54) BREATHABLE DIAPER BACKSHEET

(71) Applicant: Colormasters, LLC, Albertville, AL (US)

(72) Inventor: Robert Estill Chambliss, Trussville, AL (US)

(73) Assignee: COLORMASTERS, LLC, Albertville, AL (US)

(*) Notice: Subject to any disclaimer, the term of this patent is extended or adjusted under 35 U.S.C. 154(b) by 431 days.

(21) Appl. No.: 16/795,207

(22) Filed: Feb. 19, 2020

(65) Prior Publication Data

US 2021/0251819 A1  Aug. 19, 2021

(51) Int. Cl.
| | |
|---|---|
| *A61F 13/514* | (2006.01) |
| *B32B 27/32* | (2006.01) |
| *B32B 27/08* | (2006.01) |
| *A61F 13/49* | (2006.01) |
| *A61L 15/18* | (2006.01) |
| *A61L 15/26* | (2006.01) |

(Continued)

(52) U.S. Cl.
CPC ............ *A61F 13/514* (2013.01); *A61F 13/49* (2013.01); *A61L 15/18* (2013.01); *A61L 15/26* (2013.01); *B32B 27/08* (2013.01); *B32B 27/18* (2013.01); *B32B 27/327* (2013.01); *A61F 2013/51026* (2013.01); *A61F 2013/51409* (2013.01); *B32B 2250/03* (2013.01); *B32B 2250/242* (2013.01); *B32B 2264/104* (2013.01); *B32B 2270/00* (2013.01); *B32B 2307/54* (2013.01); *B32B 2307/724* (2013.01); *B32B 2307/726* (2013.01); *B32B 2555/02* (2013.01)

(58) Field of Classification Search
None
See application file for complete search history.

(56) References Cited

U.S. PATENT DOCUMENTS

| | | |
|---|---|---|
| 6,610,163 B1 | 8/2003 | Mathis |
| 7,862,887 B2 | 1/2011 | Chambliss et al. |
| 9,492,332 B2 | 11/2016 | Cancio et al. |

(Continued)

FOREIGN PATENT DOCUMENTS

| | | |
|---|---|---|
| EP | 1946734 A1 | 7/2008 |
| WO | 2000023509 | 4/2000 |
| WO | 2009094506 A1 | 7/2009 |

OTHER PUBLICATIONS

Westlake Chemical Corporation; Westlake Polymers SC74858 Linear Low Density Polyethylene datasheet; Houston, TX.

(Continued)

*Primary Examiner* — Samir Shah
(74) *Attorney, Agent, or Firm* — Ryan Letson; Jessica Zurlo; Bradley Arant Boult Cummings LLP

(57) ABSTRACT

A breathable thermoplastic polymer film may be produced and adapted for use as a breathable diaper backsheet. The film may include a blend of LLDPE, mLLDPE and calcium carbonate, and may have improved tear strength and melt strength such that instances of tears or break offs during the machine direction orientation portion of the production process are significantly reduced or eliminated. In addition, the film may have sufficient tear strength to permit omission of CDI processing needed to strengthen weaker prior art films. In this regard, undesired streaking of colors or printed aspects of the film may be reduced or avoided completely.

13 Claims, 2 Drawing Sheets

(51) Int. Cl.
B32B 27/18 (2006.01)
A61F 13/51 (2006.01)

(56) References Cited

U.S. PATENT DOCUMENTS

2004/0146226 A1    7/2004  Wolak et al.
2007/0260016 A1*  11/2007  Best .................. B32B 27/32
                                                525/240
2012/0237746 A1    9/2012  O'Donnell
2017/0152377 A1*   6/2017  Wang .................. B32B 7/00
2018/0140470 A1    5/2018  Cancio et al.

OTHER PUBLICATIONS

ExxonMobil; Enable 2705MC Performance Polymer Product Datasheet; Sep. 1, 2018.

* cited by examiner

BREATHABLE DIAPER BACKSHEET

BACKGROUND

Field

The present disclosure relates generally to engineered thermoplastic films, and specifically an ultra-low melt index interactive two-factorial component blend for use therewith.

Background

Films made of thermoplastics are generally flexible and breathable even in small thickness ranges. This makes thermoplastic thin films suitable for use in various applications across various types of industries and products.

For example, thermoplastic thin films are often used to make garments and wearable items. Hygienic items, such as infant and adult diapers, surgical gowns and drapes, coveralls and other disposable garments commonly have thermoplastic thin films. For such items, moisture vapor transmission and ability to adapt to the wearer's movements are important features to keep the wearer comfortable during use. Thus, thermoplastic films that can maintain breathability while serving as a barrier against leakage are generally desirable.

In order to achieve desired breathability, thermoplastic resins can be mixed with calcium carbonate. A film made with a mixture of thermoplastic resin and calcium carbonate may have increased breathability because of small voids in the film surrounding the calcium carbonate molecules. These voids achieve improved breathability for the film by allowing moisture and air to pass through. Accordingly, applications in which a high moisture vapor transmission rate (MVTR) is desired may require production of a film with high loadings of calcium carbonate. While this increase of calcium carbonate improves breathability, it also significantly weakens a film's tear strength. Some films incorporate thermoplastic resins with higher tensile strength in an effort to make the film more tear resistant. However, thermoplastic resins previously used to produce film have had higher melt indices and reduced melt strength.

Thermoplastic films are generally made using a cast process. In such a cast film process, a thermoplastic blend is heated until it melts, and is then extruded onto a chill roller. The molten blend cools and forms solid film as it passes over the cool roller. Then, the film may be stretched using a machine direction orientation (MDO) process in order to achieve improved tensile strength for the film. An example technique involves heating the film until it softens, then stretching the film over rollers in an MDO unit. However, conventional films have a tendency to break from stretching or tear from heating during the MDO process because of reduced melt strength. When a break-off or hole occurs during the MDO process, the damaged film must be manually cleared from the line and the process generally must be restarted. This can cause significant production waste and downtime while the broken film is cleared and the process is restarted. To counteract this, workers may be positioned at various points on the production line to react in case the film breaks off, tears, loses trim or otherwise. This requires devotion of significant human resources to the film making process.

A cross-direction interdigitated (CDI) process may be used to further stretch a film to add breathability and improve strength. Unfortunately, CDI processes generally result in undesired streaking of any colored or printed portions of film being processed.

Characteristics of existing thermoplastic films have made reliable thermoplastic film production very difficult. Improved techniques for producing thin thermoplastic films are generally desirable.

BRIEF DESCRIPTION OF THE DRAWINGS

The above and other features of the present disclosure, its nature and various advantages will be more apparent upon consideration of the following detailed description, taken in conjunction with the accompanying drawings in which.

DETAILED DESCRIPTION

A. Definitions

Figure 1:
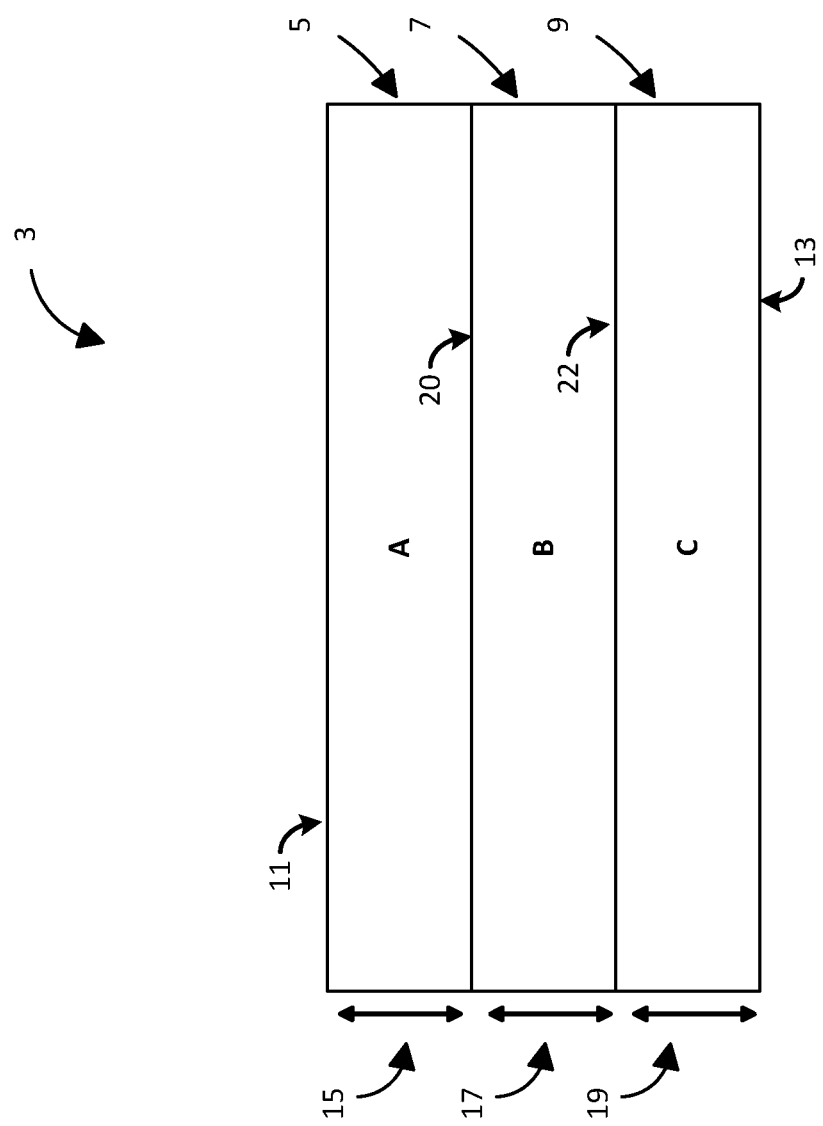
FIG. 1 shows an exemplary breathable film in accordance with some embodiments of the present disclosure.

Unless otherwise defined, all terms (including technical and scientific terms) used herein have the same meaning as commonly understood by one of ordinary skill in the art of this disclosure. It will be further understood that terms, such as those defined in commonly used dictionaries, should be interpreted as having a meaning that is consistent with their meaning in the context of the specification and should not be interpreted in an idealized or overly formal sense unless expressly so defined herein. Well known functions or constructions may not be described in detail for brevity or clarity.

The terms "about" and "approximately" shall generally mean an acceptable degree of error or variation for the quantity measured given the nature or precision of the measurements. Typical, exemplary degrees of error or variation are within 20 percent (%), preferably within 10%, and more preferably within 5% of a given value or range of values. Numerical quantities given in this description are approximate unless stated otherwise, meaning that the term "about" or "approximately" can be inferred when not expressly stated.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments.

The terminology used herein is for the purpose of describing particular embodiments only and is not intended to be limiting. As used herein, the singular forms "a", "an" and "the" are intended to include the plural forms as well, unless the context clearly indicates otherwise.

Spatially relative terms, such as "under", "below", "lower", "over", "upper" and the like, may be used herein for ease of description to describe one element or feature's relationship to another when the apparatus is right side up.

The terms "first", "second", and the like are used herein to describe various features or elements, but these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present disclosure.

Terms such as "at least one of A and B" should be understood to mean "only A, only B, or both A and B." The same construction should be applied to longer list (e.g., "at least one of A, B, and C").

In some places reference is made to standard methods, such as but not limited to methods of measurement. It is to be understood that such standards are revised from time to time, and unless explicitly stated otherwise reference to such standard in this disclosure must be interpreted to refer to the most recent published standard as of the time of filing.

"LLDPE" may refer to linear low density polyethylene, CAS No. 9002-88-4. As used herein, LLDPE refers to linear copolymers of ethylene and an α-olefin, such as butene, hexene, or octene. Examples of substances to which LLDPE may refer in the context of this document include HIFOR Xtreme® series polymers produced by Westlake Chemical Corporation, including one or more of grades SC74858, SC74844, and SC74853, or other products having a melt index of 0.5 g/10 min. or approximately 0.5 g/10 min. and density of 0.917 g/cm$^3$ or approximately 0.917 g/cm$^3$. Other polymers having similar characteristics may be suitable substitutes in some embodiments.

"mLLDPE" may refer to metallocene-catalyzed linear low density polyethylene, CAS No. 25213-02-09. By the term "metallocene-catalyzed linear low density polyethylene," it is meant a copolymer of ethylene and an α-olefin, polymerized using a metallocene catalyst. Examples of substances to which mLLDPE may refer in the context of this document include Enable™ series polymers produced by ExxonMobil Corporation, including one or more of Enable 2705MC and Enable 3505MC, other products having a having a melt index of 0.5 g/10 min. or approximately 0.5 g/10 min. and density of 0.927 g/cm$^3$ or approximately 0.927 g/cm$^3$. Other polymers having similar characteristics may be suitable substitutes in some embodiments.

"CaCO$_3$" may refer to calcium carbonate, CAS No. 471-34-1, CAS No. 1317-65-3 or similar. Calcium carbonate may be added to the substances herein such as in a resin comprising CaCO$_3$. Examples of substances to which CaCO$_3$ may refer in the context of this document include calcium carbonate concentrates produced by Standridge Color Corporation, including one or more of CaCO$_3$ 80948 concentrate or other products having a having a melt index of 0.8 g/10 min. or approximately 0.8 g/10 min. and density of 1.8 g/cm$^3$ or approximately 1.8 g/cm$^3$. CaCO$_3$ may have a D50 particle size (e.g., 50% point of diameter) of approximately 2 μm; alternatively, between approximately 2 μm and approximately 5 μm. Other substances having similar characteristics may be suitable substitutes in some embodiments.

"Melt index (MI)" may refer to a measure of the ease of flow of the melt of a thermoplastic polymer. Melt index may be measured in grams flowing per ten-minute time interval (g/10 min.) according to methods described in relevant editions of ASTM D1238, approved August 2013 and ISO 1133 published December 2011 and revised February 2012.

B. Breathable Diaper Backsheet Film and Production

FIG. 1 shows an exemplary breathable film 3 in accordance with some embodiments of the present disclosure. A breathable thermoplastic polymer film 3 may be produced and adapted for use as a breathable diaper backsheet. In one embodiment, the film 3 may comprise a blend of LLDPE, mLLDPE, and calcium carbonate, and may have improved tear strength and melt strength such that instances of tears or break offs during the machine direction orientation portion of the production process are significantly reduced or eliminated. In addition, the film 3 may have sufficient tear strength to permit omission of CDI processing needed to strengthen weaker prior art films. In this regard, undesired streaking of colors or printed aspects of the film 3 may be reduced or avoided completely. This is important because, in some embodiments, the film 3 may be incorporated in a disposable garment, such as a diaper, where characteristics of the garment are color coded.

A film 3 are useful for a variety of purposes, including, for example, use in personal hygiene products such as disposable absorbent products. Non-limiting examples include diapers, training pants, adult incontinence pads and pants, swimwear, sanitary napkins, tampons, pantiliners, etc. In one embodiment, the present invention is related to an absorbent article comprising the films described herein. In one embodiment, the absorbent article is a diaper.

A film 3 of the present invention may be suitable for use as diaper backsheets or as ears (closure tabs), and may be formed into pouches for packaging, wrapping products such as personal hygiene items, as well as foods such as sandwiches, fruits, vegetables and the like, and breathable poly bags such as breathable diaper poly bags. Other non-limiting examples of articles in which the films of the present invention may be used include building applications, such as roofing and wall linings, and backsheets for flooring and carpeting.

The film 3 may have a basis weight from approximately 12 to approximately 14 grams per square meter (gsm), alternatively from approximately 10 gsm to approximately 16 gsm; alternatively, less than approximately 14 gsm.

The film 3 shown by FIG. 1 comprises three layers 5, 7, and 9, each comprising a thermoplastic blend. Although the film 3 of FIG. 1 comprises three layers, in some embodiments, the film may comprise as few as one layer (e.g. monolayer) or more than three layers, up to approximately 10 layers, or other numbers of layers. The film 3 has two outer surfaces 11, 13 which may be outermost surfaces of layer 5 and layer 9. As shown by FIG. 1, in some embodiments, the layer 5 may be arranged on or adjacent to layer 7, and layer 7 may be arranged on or adjacent to layer 9. Each of layer 5 and layer 7 may be outer "skin" layers of the film 3, while layer 9 may be a core layer of the film 3. Other arrangements are possible in other embodiments.

Layer 5 may have a thickness 15 of between approximately 0.0015 millimeters (mm) and approximately 0.003 mm, although in some embodiments, a thickness of layer 5 may be between approximately 0.0012 mm and approximately 0.0038 mm; between approximately 0.001 mm and approximately 0.004 mm; between approximately 0.0008 mm and approximately 0.0045 mm; or between approximately 0.0006 mm and approximately 0.005 mm. Layer 5 may have a basis weight that is approximately 10% to approximately 20% of a total basis weight of the film 3. In some embodiments, layer 5 may have a basis weight that is approximately 15% of a total basis weight of film 3.

Layer 7 may have a thickness 17 of between approximately 0.009 millimeters (mm) and approximately 0.017 mm although in some embodiments, a thickness of layer 7 may be between approximately 0.0083 mm and approximately 0.011 mm; between approximately 0.008 and approximately 0.010 mm; between approximately 0.007 mm and approximately 0.009 mm; or between approximately 0.006 mm and approximately 0.008 mm. Layer 7 may have a basis weight that is approximately 60% to approximately 80% of a total basis weight of the film 3. In some embodiments, layer 7 may have a basis weight that is approximately 70% of a total basis weight of the film 3.

Layer 9 may have a thickness 19 of between approximately 0.0015 millimeters (mm) and approximately 0.003 mm, although in some embodiments, a thickness of layer 9 may be between approximately 0.0012 mm and approximately 0.0038 mm; between approximately 0.001 mm and approximately 0.004 mm; between approximately 0.0008 mm and approximately 0.0045 mm; or between approximately 0.0006 mm and approximately 0.005 mm. Layer 9 may have a basis weight that is approximately 10% to approximately 20% of a total basis weight of the film 3. In some embodiments, layer 9 may have a basis weight that is approximately 15% of a total basis weight of the film 3.

In some embodiments, each of the outermost layers of film 3 (e.g., "skin" layers 5 and 9) may have approximately the same thickness. As an example, in some embodiments, layer 5 may have a thickness that is approximately 15 percent of an overall thickness of the film 3; layer 7 may have a thickness that is approximately 70 percent of an overall thickness of the film 3; layer 9 may have a thickness that is approximately 15 percent of an overall thickness of film 3. A thickness of one or more layers of film 3, including layers 5, 7, and 9, may be varied as desired to achieve the functionality ascribed herein to film 3.

In addition, the film has two interfaces, 20 and 22. The interfaces may generally correspond to a boundary between adjacent layers. Interface 20 may correspond to a boundary of layer 5 and layer 7, and interface 22 may correspond to a boundary of layer 7 and 9. A number of interfaces of the film 3 may affect aspects of the film 3, such as tear strength and optical performance (e.g., clarity, haze, gloss, etc.). As a result, although a film 3 may have various numbers of interfaces based on a number of layers of film 3, in some preferred embodiments, the film 3 comprises two interfaces 20 and 22.

The film 3 of FIG. 1 is shown as having a particular length, but a film according to some embodiments of the present disclosure may be produced to have various desired lengths. As described further below, the components of film 3 may be heated, extruded and blown to form a film sheath, bubble or similar structure. Length of the film 3 may be related to an amount of resin or material that is extruded and blown; accordingly, length of film 3 may be based on an amount (e.g., volume) of constituent film components (e.g., resins) which are melted, extruded and blown to form film 3.

The film 3 may have various thicknesses (e.g., sum of layer thicknesses 15, 17 and 19), but in some embodiments, the film 3 may be between approximately 0.01 mm and approximately 0.02 millimeters (mm) thick. In other embodiments, the thickness of film 3 may be between approximately 0.013 mm and approximately 0.017 mm. Thicknesses of layers 5, 7 and 9 shown in FIG. 1 are not necessarily to scale, and in some embodiments, a thickness of each of the constituent layers 5, 7, and 9 may vary.

The film 3 according to some embodiments of the present disclosure may have a moisture vapor transmission rate ("MVTR"). The term, "moisture vapor transmission rate," refers to the measure of the passage of water vapor through a substance. The film 3 according to some embodiments has a MVTR of approximately 2,000 gsm/day; alternatively, at least about 500 gsm/day; alternatively, between about 500 gsm/day and 2,000 gsm/day; alternatively, between approximately 2,000 gsm/day and 7,000 gsm/day. In some embodiments, a film 3 may have an MVTR of less than 7,000 gsm/day; alternatively, the film 3 may have a MVTR of between approximately 4,000 gsm/day and approximately 6,000 gsm/day.

The film 3 according to some embodiments of the present disclosure may have a melt index of about 0.5 g/10 min.; alternatively, about 0.1 g/10 min. to about 0.5 g/10 min.; alternatively, about 0.3 g/10 min. to about 0.5 g/10 min.; alternatively, about 0.5 g/10 min. to 0.7 g/10 min; alternatively, about 0.5 g/10 min. to about 0.9 g/10 min.

The film 3 according to some embodiments of the present disclosure may have a tensile strength (MD—machine direction) of approximately 3,000 MPa to approximately 6,000 MPa; alternatively, approximately 4,000 MPa to approximately 5,000 MPa. The film 3 according to some embodiments of the present disclosure may have a tensile strength (TD—transverse direction) of approximately 500 MPa to approximately 2,000 MPa; alternatively, approximately 750 MPa to approximately 1,500 MPa.

In some embodiments, the film 3 (e.g., one or more of layer 5, 7 or 9) may be a composition comprising one or more of a structural polymer fraction and plasticizer polymer fraction. In some embodiments, one or more of the first thermoplastic polymer, second thermoplastic polymer may serve as a percentage of a structural polymer fraction of the composition. Percentages of the structural polymer fraction which the one or more thermoplastic polymers make up may be varied as desired to achieve the functionality ascribed to the film 3 herein. Alternatively, either or one or more of the first thermoplastic polymer, second thermoplastic polymer may serve as a percentage of a plasticizer polymer fraction of the film 3. Percentages of the plasticizer polymer fraction which the one or more thermoplastic polymers make up may be varied as desired to achieve the functionality ascribed to the film 3 herein.

The film 3 according to some embodiments of the present invention may comprise one or more thermoplastic polymers. Suitable polymers for the films include, but are not limited to, polyolefins, for example, polyethylene homopolymers and copolymers, polypropylene, polypropylene homopolymers and copolymers, functionalized polyolefins, polyesters, poly(ester-ether), polyamides, including nylons, poly(ether-amide), polyether sulfones, fluoropolymers, polyurethanes, and mixtures thereof. Polyethylene homopolymers include those of low, medium or high density and/or those formed by high pressure or low-pressure polymerization. Polyethylene and polypropylene copolymers include, but are not limited to, copolymers with C4-C8 alpha-olefin monomers, including 1-octene, 1-butene, 1-hexene and 4-methyl pentene. The polyethylene may be substantially linear or branched, and may be formed by various processes known in the art using catalysts such as Ziegler-Natta catalysts, metallocene or single-site catalysts or others widely known in the art. Examples of suitable copolymers include, but are not limited to, copolymers such as poly (ethylene-butene), poly(ethylene-hexene), poly(ethylene-octene), and poly(ethylene-propylene), poly(ethylene-vinylacetate), poly(ethylene-methylacrylate), poly(ethylene-acrylic acid), poly(ethylene-butylacrylate), poly(ethylene-propylenediene), poly(methyl methacrylate) and/or polyolefin terpolymers thereof. In one embodiment, the films comprise polyethylene, polypropylene, and combinations thereof. Suitable examples of thermoplastics present in some preferred embodiments of the film 3 are HIFOR Xtreme super hexene linear low-density polyethylene (LLDPE) by Westlake Chemical Corporation, and Enable bimodal metallocene linear low-density polyethylene (m-LLDPE) by ExxonMobil Corporation. Compositions comprising other components are possible in other embodiments.

In some embodiments, the one or more thermoplastic polymers may comprise one or more of: linear low-density polyethylene (LLDPE), super hexene linear low-density polyethylene (LLDPE), such as Westlake HIFOR® Xtreme; bimodal metallocene linear low-density polyethylene (mLLDPE), such as Exxon Enable™; or various combinations thereof. The linear low-density polyethylene present in one or more layers of film 3 may have a melt index of about 0.5 g/10 min.; alternatively, about 0.1 g/10 min. to about 0.5 g/10 min.; alternatively, about 0.3 g/10 min. to about 0.5 g/10 min.; alternatively, about 0.5 g/10 min. to 0.7 g/10 min; alternatively, about 0.5 g/10 min. to about 0.9 g/10 min. Bimodal metallocene linear low-density polyethylene present in a film 3 may have a melt index of about 0.5 g/10 min.; alternatively, about 0.1 g/10 min. to about 0.5 g/10 min.; alternatively, about 0.3 g/10 min. to about 0.5 g/10 min.; alternatively, about 0.5 g/10 min. to 0.7 g/10 min; alternatively, about 0.5 g/10 min. to about 0.9 g/10 min.

In some embodiments the linear low-density polyethylene present in one or more layers of film 3 may have a tensile strength at break of about 60 MPa; alternatively, about 50 MPa to about 60 MPa. Bimodal metallocene linear low-density polyethylene present in a film 3 may have a tensile strength at break of about 59 MPa; alternatively, about 50 MPa to about 60 MPa.

In some embodiments, the aforementioned thermoplastic polymers may be present in the film 3 or in individual layers (e.g., layers 5, 7, or 9) in an amount varying from about 0% to 95%; alternatively, from about 0% to about 45%; alternatively from about 10% to about 20%; alternatively from about 25% to about 50%, and alternatively from about 1% to about 10%. Additional percentages of which the aforementioned thermoplastic polymers may be present in the film 3 or in its individual layers are shown in Tables 1-3. Other percentages may be possible in other embodiments.

In some embodiments, any of the aforementioned thermoplastic polymers may be present in the film 3 or in individual layers with respect to another of the aforementioned thermoplastic polymers in a ratio of about 60% to about 40% (e.g., 3:2); alternatively, about 0% to about 95%; alternatively, about 65% to about 35%; alternatively, about 55% to about 45%; alternatively, about 1% to about 10%. As an example, in a preferred exemplary embodiment, a ratio of LLDPE to mLLDPE may be about 60% (LLDPE) to 40% (mLLDPE), or 3:2. Additional ratios of which the aforementioned thermoplastic polymers may be present in the film 3 or in its individual layers with respect to one or more of the aforementioned layers are shown in Tables 1-3. Other ratios may be possible in other embodiments.

The film 3 according to some embodiments of the present disclosure may include a breathability agent, such as calcium carbonate ($CaCO_3$) or similar composition. As used herein, a "breathability agent," may refer to one or more substances or compounds used to enhance the moisture vapor permeability (or "breathability") of the film 3. A suitable example of a breathability agent may be $CaCO_3$. An example of a commercially available calcium carbonate is $CaCO_3$ 80948 by Standridge Color Corporation.

In some embodiments, the breathability agent may be present in the film 3 or in individual layers in an amount of at least 60% by weight of the total weight of the film 3. In another embodiment, the breathability agent may be present in the film 3 or in individual layers in an amount of at least 70% by weight of the total weight of the film 3. In still another embodiment, the breathability agent may be present in the film 3 or in individual layers in an amount of at least 80% by weight of the total weight of the film 3.

The film 3 according to some embodiments of the present disclosure may include one or more colorization compositions for colorizing the film. As noted above, color may be used in various applications to indicate attributes of an article that includes film 3. As an example, disposable garments may include a film 3 that is colored to indicate garment size. In this regard, one or more layers 5, 7, or 9 of film 3 may comprise a colorization component. In some embodiments, a color may be provided by one or more or a combination of: the breathability agent (e.g., calcium carbonate) or a thermoplastic polymer composition (e.g., a composition comprising one or more of LLDPE, mLLDPE, etc.) of the film 3.

Preferred additives include color concentrates, neutralizers, process aids, lubricants, stabilizers, hydrocarbon resins, antistatics, and antiblocking agents. A color concentrate may be added to yield a colored layer, an opaque layer, or a translucent layer. Preferred color concentrates include color formulations, including black, white, and other colors suitable for the film of the present invention. Preferred color concentrates include Ampacet® white PE masterbatch, available from Ampacet Corporation (Tarrytown, N.Y.). The carrier resin of Ampacet® white PE masterbatch is a LLDPE having a melt index of 20 g/10 min and a density of 0.92 g/cc. This concentrate has a nominal specific gravity of 2.06, a melt index of 3-23 g/10 min, and nominally contains 75% ash. Another preferred color concentrate includes Ampacet® white HDPE masterbatch, the carrier resin of which is a HD/LLDPE having a nominal melt index of 10 g/10 min and a density of 0.96 g/cc. This concentrate has a nominal specific gravity of 1.54, a melt index of 9-15 g/10 min, and a pigment composed of 50% $TiO_2$.

In some embodiments, one or more layers 5, 7, and 9 of film 3 may comprise a polyethylene colorization component. In some embodiments, the colorization component may be a polyethylene colorization component produced by the Standridge Color Corporation, such as SCC code: 91223 MDO Blue color concentrate. Example colorization agents and percentages of such components as a fraction of film 3 are described further in Tables 1-3.

The film 3 according to some embodiments of the present disclosure may include one or more of various optional components, such as fillers, plasticizers, compatibilizers, draw down polymers, processing aids, anti-blocking agents, viscosity-reducing polymers, and the like. Other additives may include pigments, dyes, antioxidants, antistatic agents, slip agents, foaming agents, heat or light stabilizers, UV stabilizers, and the like. Additional and optional components that may be present in some embodiments of the film 3 are included at Col. 4, line 43 to Col. 5, line 46 of U.S. Pat. No. 7,862,887, which portions are incorporated herein by reference.

Figure 2:
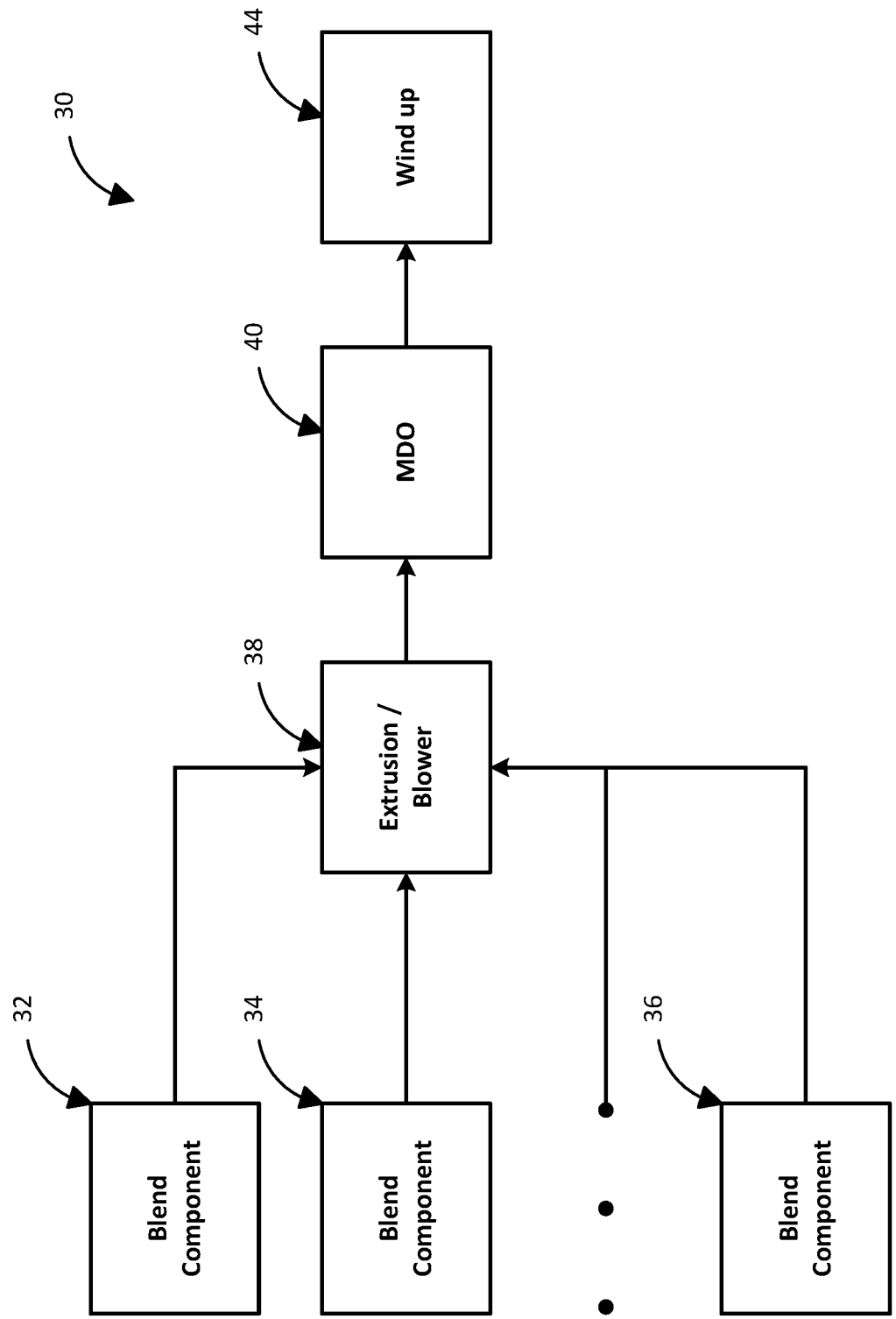
FIG. 2 shows an exemplary process for producing an exemplary breathable film in accordance with some embodiments of the present disclosure.

FIG. 2 shows an exemplary process for producing an exemplary breathable film in accordance with some embodiments of the present disclosure. The multilayer film 3 of the present invention may be produced by various methods used in producing multilayer films, including coextrusion and extrusion techniques. For example, the film 3 may be formed by coextrusion and blown to form a bubble. Blend components 32-36 may be melted and plasticized to form individual layers. Streams of individual layer materials may be fed into a coextrusion die, and while in the die, the layers may be combined in a desired arrangement, after which they emerge from the die in a single multilayer film of polymeric material.

As an example of the techniques that may be used to produce film, conventional methods may be suitable and may be useful in producing film 3 such as by coextrusion techniques and lamination techniques.

Coextrusion techniques include methods which include the use of a feed block with a standard die, a multimanifold die such as a circular die for blown bubble film, as well as a multimanifold die such as used in forming multilayer films for forming flat cast films and cast sheets. One particular advantage of coextruded films is in the formation of a multilayer film in one process step by combining molten layers of each of the film layers of fluoropolymer, tie layer composition, and thermoplastic polymer, as well as optionally more film layers, into a unitary film structure.

In order to produce a multilayer film by a coextrusion process, it is necessary that the constituents used to form each of the individual films be compatible in the film extrusion process. What is to be understood by the term "compatible" in this respect is that the film-forming compositions used to form the films have melt properties which are sufficiently similar so to allow coextrusion; melt properties of interest include melting points, melt flow indices, apparent viscosity, as well as melt stability. It is important that such compatibility be present so to assure the production of a multilayer film having good adhesion and relatively uniform thickness across the width of the film being produced. As is known in the art, film-forming compositions which are not sufficiently compatible to be useful in a coextrusion process frequently produce films having poor interfacial lamination, poor physical properties as well as poor appearance. In the practice of the present invention, the above-noted factors which are useful in determining compatibility may be determined, and once polymers having desirable physical properties are selected, experimental trials may be conducted in order to determine the optimal combination of relative properties in adjacent layers. If a coextrusion process is used, it is important that the constituents used to form a multilayer film be compatible within a relatively close temperature range, so they may be extruded through a common die. It has been found that the variation of the quantity of the modified polyolefin within the tie layer composition provides an adhesive layer forming composition which is of sufficiently high melt viscosity, especially in the preferred range of compositions described above, to be particularly useful in a coextrusion process with a fluoropolymer film forming composition, and with a PETG film forming composition.

Alternatively, the multilayer films of the present invention can be produced by a lamination technique. Lamination techniques are well known in the art. Such lamination techniques involve forming a multilayer film structure from pre-fabricated film plies. The basic methods used in film laminating techniques are fusion, wet combining, and heat reactivation. Fusion is a method of laminating two or more film plies using heat and pressure without the use of adhesives. This method can only be used where the films being laminated are comprised of polymers that readily form interfacial adhesion. Wet combining and heat reactivation are utilized in laminating incompatible films using adhesive materials. Further details of lamination techniques are disclosed, for example, in the Modern Plastics Encyclopedia, Vol. 57, No. 10A, pp 345-348, McGraw Hill, October 1980.

Blend components 32-36 may represent one or more constituent substances of a composition used to make film 3. Example blend components 32-36 include thermoplastic polymer resin, breathability agent, or other substances that may be received for heating and extrusion. Although a particular number of blend components 32-36 are shown in FIG. 2, the foregoing is not limiting, and in some embodiments, various numbers of substances may be introduced for film production purposes based on substances present in a desired film 3. Example quantities of blend components for producing a film 3 include about 1 to about 4; alternatively, about 3 to about 6; alternatively, about 2 to about 4; alternatively, about 0 to about 3; alternatively, about 4 to about 10; or alternatively, about 1 to about 5.

The components 32-36 may begin film production processing in various forms, such as solid rods, pellets, sheet, chunks, or otherwise. The blend components 32-36 may be held in various containers, such as hoppers, vats, etc., and may be dosed or fed to extrusion/blower section 38 for melting, extrusion, and blowing of the extruded blend into a bubble. A rate at which material from each of the blend component storage containers may vary, and may be based on various factors, such as a desired material extrusion rate or similar.

Coextrusion of a film 3 may be conducted at temperatures of from about 400° F. to about 510° F., although various other temperatures and ranges are possible based on melting points of the respective blend components 32-36. Coextrusion techniques may include the use of a feed block with a standard die, a multi-manifold die, such as a circular die, as well as a multi-manifold die such as used in forming flat cast films and cast sheets. Other techniques for extrusion may be possible in other embodiments.

In some embodiments, a film 3 may be made by blown film coextrusion. Blend components 32-36 may be fed to the extrusion and blowing portion 38 for coextrusion and blowing of the film into a bubble or sheath. In the extrusion and blowing portion 38, components 32-36 are combined using extruders for mixing, melting, measuring and preparing the film for further extrusion as a layer of film 3. As an example, each the blends of each of layer 5, 7, and 9 may be mixed and extruded in a similar manner to form the respective layers 5, 7, and 9. The extrusion can be performed using various techniques, such as a die. This may be repeated for additional layers of film 3, until extrusion of each of the desired layers of film 3 has completed.

After extrusion, the film 3 is further formed using a blown film apparatus. The apparatus may comprise a multi-manifold circular die head having concentric circular orifices. As part of an extrusion/blowing process 38 in accordance with some embodiments of the present disclosure, a film 3 may be blown out of the die as molten plastic, quenched by air to a solid state, and cooled to room temperature.

As an example, a first layer of film 3 may be extruded while in a melted state through a circular die of the apparatus. Each consecutive layer of film 3 may be subsequently extruded in a desired arrangement, such as on either side of the first layer (e.g., by selecting one or more 0.20 additional circular dies concentric with a first circular die). Next, a gas, typically air, is blown through a central portion of the circular die head and into an interior portion of the extruded film 3 to form a bubble. In this regard, the bubble may expand individual layers of film 3.

Thereafter, the bubble may be collapsed onto itself (e.g., using a roller or other component of the blown film process) to form a substantially flattened sheath. The portions of the flattened sheath may be cut along opposing edges to form a pair of multilayer films. Usually, the pair of attached multilayer films are then cut apart at one or more of the edges and separated into a pair of multilayer films that can be spooled or wound onto a roll.

After the film 3 is blown and cut, it may pass downstream to one or more machine direction orientation (MDO) sections as part of MDO process 40. Exemplary machine direction orientation techniques are more fully described at paragraphs [0070]-[0083] of U.S. Pat. App. Pub. No. US 2018/0140470 A1, which are incorporated herein by reference.

Sections of the MDO process 40 may stretch the film in the machine direction while still avoiding significant MD orientation. A stretching section of MDO process 40 may include heated rollers, followed by one or more stretching rollers and/or one or more cooling rollers. Heated rollers may heat film 3 to a desired temperature that is sufficient to allow stretching of the film, but is below a melt temperature. In some embodiments, a temperature at which the film may be heated may be from about 50° C. to about 90° C., alternatively from about 40° C. to about 100° C. Quantities and arrangements of heated rollers and chilled rollers MDO process may vary, and MDO process 40 may comprise one or more additional sets of stretching rollers, heated rollers, cooling rollers or other components in order to achieve desired characteristics of film 3 (e.g., porosity, opacity). As an example, by stretching in MDO process 40, microscopic voids may be pulled around $CaCO_3$ present in preferred embodiments of film 3. The stretching rollers, heated rollers, and cooling rollers of MDO process 40 may be arranged as desired within the MDO process 40 and can be arranged in various combinations and quantities to achieve desired MDO of a film 3. Downstream of the stretching section of MDO process 40, a film 3 may be annealed by an annealing section. In this section, the film 3 travels through consecutive cooled and heated rolls. This process may set mechanical properties of the film.

As indicated above, a film 3 produced according to some embodiments of the present disclosure may have sufficient breathability without requiring the film to be stretched in a CDI processing section. In contrast to the techniques described in U.S. Pat. No. 9,492,332, in some preferred embodiments, no CDI section is needed to achieve improved tensile strength and tear strength of the films 3. In this regard, streaking of colorized embodiments of film 3 caused as part of a CDI process may be eliminated.

Note that rates of speed at which one or more rollers of the MDO process 40 are operating may progressively increase based on a position of the one or more rollers within the MDO process 40. As an example, a first roller may have a first rotational speed, $\omega_1$ (e.g., rad/s) and first tangential speed, $v_1$ (e.g., m/s). A second roller further downstream in the MDO process 40 may have a second rotational speed, $\omega_2$ and second tangential speed, $v_2$. In some embodiments, the second rotational speed, $\omega_2$ and second tangential speed, $v_2$ may be greater than the first rotational speed, $\omega_1$ and first tangential speed, $v_1$. Subsequent rollers within the stream of MDO process 40 may have a rotational speed and tangential speed that is greater than rotational speed, $\omega_2$ and tangential speed, $v_2$.

Following the MDO process 40, film 3 may be rolled, wound or spooled into rolls as part of wind up process 44 using one or more winding rollers. The wind up process 44 may allow for film 3 at room temperature to be formed into rolls for transportation and storage. Other techniques for winding a film 3 may be used in other embodiments.

C. Examples

Example films produced in accordance with some embodiments of the present disclosure are shown in Tables 1-3. Each of the exemplary films of Tables 1-3 has three layers: Layer A (layer 5), Layer B (layer 7), and Layer C (layer 9). As stated previously, other numbers of layers are possible in other embodiments. Each of the tables shows respectively, in columns from left to right: 1) Layer identifier; 2) presence of polymeric compositions in the film 3 as a weight percentage of the film 3 thickness; 3) individual thermoplastic polymeric resins types present in the film by layer; 4) presence of individual substances in thermoplastic polymeric compositions of the film 3 as a weight percentage of the composition the layer; 5) supplier name by individual thermoplastic polymer; 6) product name by substance; 7) substance type identifier; 8) slip agent (ppm); 9) antiblock agent (ppm); 10) Melt Index (g/10 min.); and 11) density (g/cm³).

Table 1 shows exemplary characteristics for a film 3 in accordance with some embodiments of the present disclosure. The film 3 of Table 1 was formed according to the method described further below with regard to FIG. 2. The film 3 of Table 1 has a basis weight of approximately 12 gsm to approximately 14 gsm. The film 3 of Table 1 has an essentially white color.

TABLE 1

| LAYER | % | RESIN | % | Supplier | Name | Type | SLIP | AB | MI | Density |
|---|---|---|---|---|---|---|---|---|---|---|
| A | 15% | SC 74858 | 44.00% | Westlake | HIFOR Xtreme | LLDPE | 0 | 0 | 0.5 | 0.917 |
|   |   | 27-05MC | 30.00% | Exxon | Enable | m-LLDPE | 0 | 0 | 0.5 | 0.927 |
|   |   | CaCO3 80948 | 25.00% | Standridge |   | Ca03 concentrate | 0 | 0 | 8.0 | 1.8 |
|   |   | BI-607 | 1.00% | Bayshore |   | PA | 0 | 0 | 8.0 | 0.93 |
| B | 70% | SC 74858 | 45.00% | Westlake | HIFOR Xtreme | LLDPE | 0 | 0 | 0.5 | 0.917 |
|   |   | 27-05MC | 30.00% | Exxon | Enable | m-LLDPE | 0 | 0 | 0.5 | 0.927 |
|   |   | CaCO3 80948 | 15.00% | Standridge |   | Ca03 conc | 0 | 0 | 8.0 | 1.8 |
|   |   | SCC 90889 | 10.00% | Standridge |   | White conc | 0 | 0 | 8.0 | 1.72 |

TABLE 1-continued

| LAYER | % | RESIN | % | Supplier | Name | Type | SLIP | AB | MI | Density |
|---|---|---|---|---|---|---|---|---|---|---|
| C | 15% | SC 74858 | 44.00% | Westlake | HIFOR Xtreme | LLDPE | 0 | 0 | 0.5 | 0.917 |
| | | 27-05MC | 30.00% | Exxon | Enable | m-LLDPE | 0 | 0 | 0.5 | 0.927 |
| | | CaCO3 80948 | 25.00% | Standridge | | Ca03 conc | 0 | 0 | 8.0 | 1.8 |
| | | BI-607 | 1.00% | Bayshore | | PA | 0 | 0 | 8.0 | 0.93 |

Table 2 shows alternative exemplary characteristics for a film 3 in accordance with some embodiments of the present disclosure. The film 3 of Table 2 was formed according to the method described further below with regard to FIG. 2. The film 3 of Table 2 has a basis weight of approximately 12 gsm to approximately 14 gsm. The film 3 of Table 2 has a white color.

TABLE 2

| LAYER | % | RESIN | % | Supplier | Name | Type | SLIP | AB | MI | Density |
|---|---|---|---|---|---|---|---|---|---|---|
| A | 15% | SC 74858 | 18.00% | Westlake | HIFOR Xtreme | LLDPE | 0 | 0 | 0.5 | 0.917 |
| | | 27-05MC | 12.00% | Exxon | Enable | m-LLDPE | 0 | 0 | 0.5 | 0.927 |
| | | CaCO3 80948 | 69.00% | Standridge | | Ca03 conc | 0 | 0 | 8.0 | 1.8 |
| | | B1-607 | 1.00% | Bayshore | | PA | 0 | 0 | 8.0 | 0.93 |
| B | 70% | SC 74858 | 18.00% | Westlake | HIFOR Xtreme | LLDPE | 0 | 0 | 0.5 | 0.917 |
| | | 27-05MC | 12.00% | Exxon | Enable | m-LLDPE | 0 | 0 | 0.5 | 0.927 |
| | | CaCO3 80948 | 70.00% | Standridge | | Ca03 conc | 0 | 0 | 8.0 | 1.8 |
| C | 15% | SC 74858 | 18.00% | Westlake | HIFOR Xtreme | LLDPE | 0 | 0 | 0.5 | 0.917 |
| | | 27-05MC | 12.00% | Exxon | Enable | m-LLDPE | 0 | 0 | 0.5 | 0.927 |
| | | CaCO3 80948 | 69.00% | Standridge | | Ca03 conc | 0 | 0 | 8.0 | 1.8 |
| | | B1-607 | 1.00% | Bayshore | | PA | 0 | 0 | 8.0 | 0.93 |

Table 3 shows alternative exemplary values for Layers 5 (Layer A), 7 (Layer B) and 9 (Layer C) in accordance with some embodiments of the present disclosure. The film 3 of Table 3 was formed according to the method described further below with regard to FIG. 2. The film 3 of Table 3 has a basis weight of approximately 12 gsm to approximately 14 gsm. The film 3 of Table 3 has a beige color.

TABLE 3

| LAYER | % | RESIN | % | Supplier | Name | Type | SLIP | AB | MI | Density |
|---|---|---|---|---|---|---|---|---|---|---|
| A | 15% | SC 74858 | 41.00% | Westlake | HIFOR Xtreme | LLDPE | 0 | 0 | 0.5 | 0.917 |
| | | 27-05MC | 28.00% | Exxon | Enable | m-LLDPE | 0 | 0 | 0.5 | 0.927 |
| | | CaCO3 80948 | 25.00% | Standridge | | Ca03 conc | 0 | 0 | 8.0 | 1.8 |
| | | SCC Cream | 5.00% | Standridge | | Beige/Cream color | 0 | 0 | 8.0 | 1.47 |
| | | BI-607 | 1.00% | Bayshore | | PA | 0 | 0 | 8.0 | 0.93 |
| B | 70% | SC 74858 | 47.00% | Westlake | HIFOR Xtreme | LLDPE | 0 | 0 | 0.5 | 0.917 |
| | | 27-05MC | 31.00% | Exxon | Enable | m-LLDPE | 0 | 0 | 0.5 | 0.927 |
| | | CaCO3 80948 | 17.00% | Standridge | | Ca03 conc | 0 | 0 | 8.0 | 1.8 |
| | | SCC Cream | 5.00% | Standridge | | Beige/cream color | 0 | 0 | 8.0 | 1.47 |
| C | 15% | SC 74858 | 41.00% | Westlake | HIFOR Xtreme | LLDPE | 0 | 0 | 0.5 | 0.917 |
| | | 27-05MC | 28.00% | Exxon | Enable | m-LLDPE | 0 | 0 | 0.5 | 0.927 |
| | | CaCO3 80948 | 25.00% | Standridge | | Ca03 conc | 0 | 0 | 8.0 | 1.8 |
| | | SCC Cream | 5.00% | Standridge | | Beige/cream color | 0 | 0 | 8.0 | 1.47 |
| | | BI-607 | 1.00% | Bayshore | | PA | 0 | 0 | 8.0 | 0.93 |

It is to be understood that any given elements of the disclosed embodiments of the invention may be embodied in a single structure, a single step, a single substance, or the like. Similarly, a given element of the disclosed embodiment may be embodied in multiple structures, steps, substances, or the like.

The foregoing description illustrates and describes the processes, machines, manufactures, compositions of matter, and other teachings of the present disclosure. Additionally, the disclosure shows and describes only certain embodiments of the processes, machines, manufactures, compositions of matter, and other teachings disclosed, but, as mentioned above, it is to be understood that the teachings of the present disclosure are capable of use in various other combinations, modifications, and environments and is capable of changes or modifications within the scope of the teachings as expressed herein, commensurate with the skill and/or knowledge of a person having ordinary skill in the relevant art. The embodiments described hereinabove are further intended to explain certain best modes known of practicing the processes, machines, manufactures, compositions of matter, and other teachings of the present disclosure and to enable others skilled in the art to utilize the teachings of the present disclosure in such, or other, embodiments and with the various modifications required by the particular applications or uses. Accordingly, the processes, machines, manufactures, compositions of matter, and other teachings of the present disclosure are not intended to limit the exact embodiments and examples disclosed herein. Any section headings herein are provided only for consistency with the suggestions of 37 C.F.R. § 1.77 or otherwise to provide organizational queues. These headings shall not limit or characterize the invention(s) set forth herein.

What is claimed is:

1. An absorbent article comprising a breathable film, wherein the breathable film comprises:
    a blend of super hexene linear low-density polyethylene and bimodal metallocene-catalyzed linear low-density polyethylene, wherein the super hexene linear low-density polyethylene and bimodal metallocene-catalyzed linear low-density polyethylene each have a melt index of about 0.3 g/10 min to about 0.5 g/10 min, wherein the super hexene linear low-density polyethylene is present in the blend in a greater amount than the bimodal metallocene-catalyzed linear low-density polyethylene; and
    a breathability agent,
    wherein the breathable film has a tensile strength of about 3,000 MPa to about 6,000 MPa when stretched using machine direction orientation.

2. The absorbent article of claim 1, wherein a ratio of the super hexene linear low-density polyethylene to the bimodal metallocene-catalyzed linear low-density polyethylene is about 3:2.

3. The absorbent article of claim 1, wherein the breathable film has a melt index of less than about 1.10 g/10 min.

4. The absorbent article of claim 1, wherein the breathable film has a melt index of less than about 0.7 g/10 min.

5. The absorbent article of claim 1, wherein the breathability agent comprises calcium carbonate, and wherein the breathability agent comprises at least 60% of the total weight of the breathable film.

6. The absorbent article of claim 1, wherein the breathable film has a basis weight of less than 14 grams per square meter (gsm).

7. The absorbent article of claim 1, wherein the breathable film has a moisture vapor transmission rate of at least 2,000 gsm/day.

8. The absorbent article of claim 1, wherein the super hexene linear low-density polyethylene is present in the blend in an amount of about 60 percent by weight and the bimodal metallocene-catalyzed linear low-density polyethylene is present in the blend in an amount of about 40 percent by weight.

9. The absorbent article of claim 1, wherein the breathability agent comprises calcium carbonate, and wherein the breathability agent is present in an amount of more than 70 percent by weight of the total weight of the breathable film.

10. A diaper backsheet comprising a film, wherein the film comprises a first layer, a second layer, and a third layer, each layer comprising:
    a blend of super hexene linear low-density polyethylene and bimodal metallocene-catalyzed linear low-density polyethylene, wherein the super hexene linear low-density polyethylene and bimodal metallocene-catalyzed linear low-density polyethylene each have a melt index of about 0.3 g/10 min to about 0.5 g/10 min, wherein the super hexene linear low-density polyethylene is present in the blend in a greater amount than the bimodal metallocene-catalyzed linear low-density polyethylene; and
    a breathability agent comprising calcium carbonate, wherein the film has a melt index less than about 0.7 g/10 min and a tensile strength of about 4,000 MPa to about 5,000 MPa when stretched using machine direction orientation.

11. The diaper backsheet of claim 10, wherein the super hexene linear low-density polyethylene and the bimodal metallocene-catalyzed linear low-density polyethylene are present in each layer in a ratio of about 3:2.

12. The diaper backsheet of claim 10, wherein each layer of the film comprises at least about 70% by weight of the breathability agent.

13. The diaper backsheet of claim 10, wherein the breathable film has a moisture vapor transmission rate of at least 2,000 gsm/day.

* * * * *